US011069060B2

(12) United States Patent
Kamei et al.

(10) Patent No.: US 11,069,060 B2
(45) Date of Patent: Jul. 20, 2021

(54) IMAGE PROCESSING APPARATUS AND RADIOGRAPHIC IMAGE DATA DISPLAY METHOD

(71) Applicant: CANON KABUSHIKI KAISHA, Tokyo (JP)

(72) Inventors: Satoshi Kamei, Tokyo (JP); Osamu Tsujii, Kawasaki (JP); Tetsuo Shimada, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 24 days.

(21) Appl. No.: 16/497,313

(22) PCT Filed: Mar. 23, 2018

(86) PCT No.: PCT/JP2018/011716
§ 371 (c)(1),
(2) Date: Sep. 24, 2019

(87) PCT Pub. No.: WO2018/180995
PCT Pub. Date: Oct. 4, 2018

(65) Prior Publication Data
US 2020/0380670 A1    Dec. 3, 2020

(30) Foreign Application Priority Data

Mar. 27, 2017    (JP) ............... JP2017-061535

(51) Int. Cl.
*G06T 7/00*    (2017.01)
*G06T 7/70*    (2017.01)
(Continued)

(52) U.S. Cl.
CPC ............ *G06T 7/0012* (2013.01); *A61B 6/032* (2013.01); *A61B 6/502* (2013.01); *G06T 7/70* (2017.01);
(Continued)

(58) Field of Classification Search
CPC ....... A61B 6/032; A61B 6/502; G06T 7/0012; G06T 7/70; G06T 11/003; G06T 2207/10116; G06T 2207/30068
See application file for complete search history.

(56) References Cited

U.S. PATENT DOCUMENTS

2014/0033126 A1*    1/2014    Kreeger ............... A61B 6/463
715/821

FOREIGN PATENT DOCUMENTS

JP    2003-310587 A    11/2003
JP    2005-65857 A    3/2005
(Continued)

OTHER PUBLICATIONS

Boulehmi,H, et al., "A New CAD System for Breast Microcalcifications Diagnosis", IJACSA, 2016, pp. 133-143, vol. 7, No. 4.

*Primary Examiner* — Mark R Gaworecki
(74) *Attorney, Agent, or Firm* — Canon U.S.A., Inc., IP Division

(57) ABSTRACT

The present invention provides an image display method that enables intuitive identification of a portion where a mammary gland region and a microcalcified region overlap each other in a radiographic captured image of a breast. The radiographic image data display method according to an aspect of the present invention includes detecting microcalcified regions and a mammary gland region in the radiographic image data, and displaying the microcalcified regions and the mammary gland region on a single screen.

8 Claims, 7 Drawing Sheets

(51) Int. Cl.
 *G06T 11/00* (2006.01)
 *A61B 6/03* (2006.01)
 *A61B 6/00* (2006.01)

(52) U.S. Cl.
 CPC ... *G06T 11/003* (2013.01); *G06T 2207/10116* (2013.01); *G06T 2207/30068* (2013.01)

(56) References Cited

FOREIGN PATENT DOCUMENTS

| | | | |
|---|---|---|---|
| JP | 2005-211439 | A | 8/2005 |
| JP | 2015-144632 | A | 8/2015 |
| JP | 2016-22143 | A | 2/2016 |
| WO | 2016/011339 | A1 | 1/2016 |

* cited by examiner

[Fig. 1]
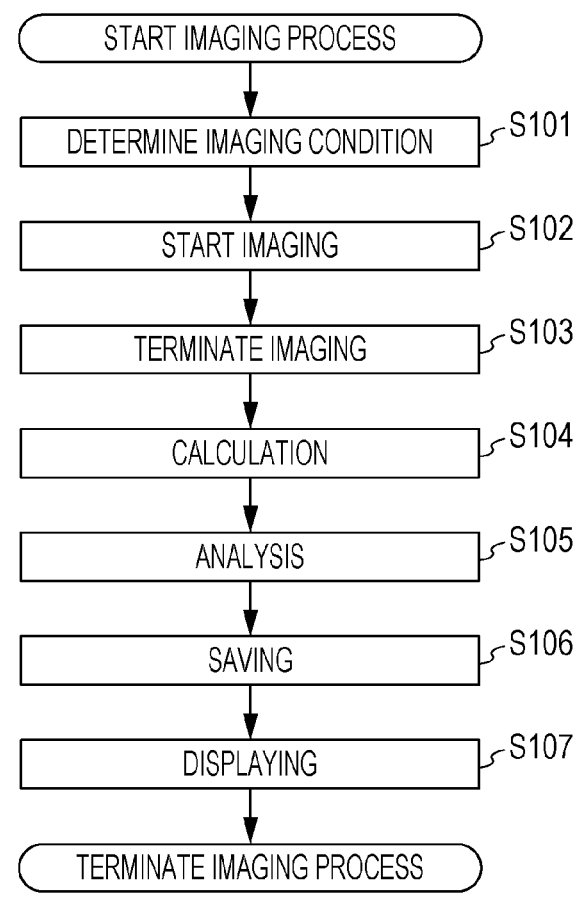

[Fig. 2A]
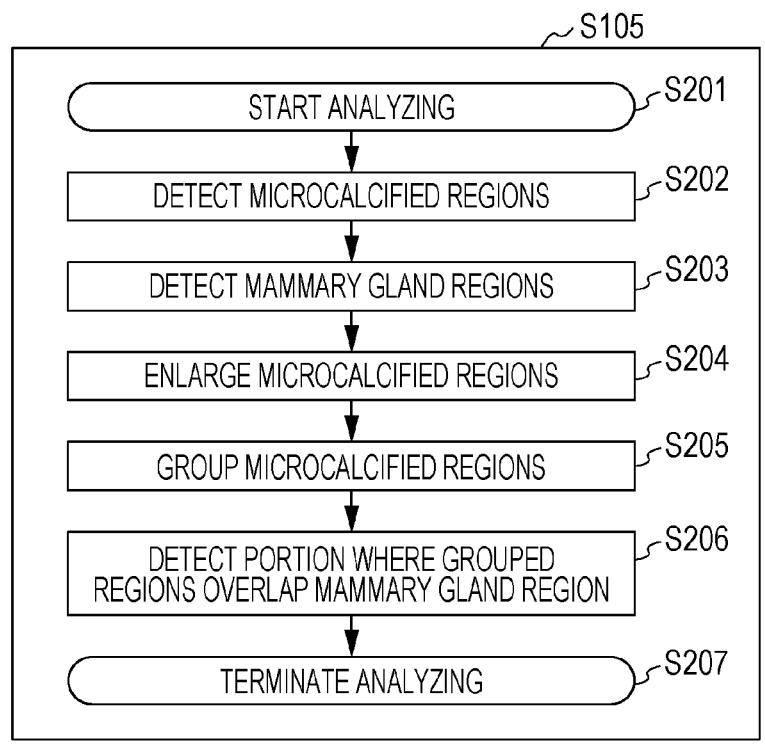

[Fig. 2B]
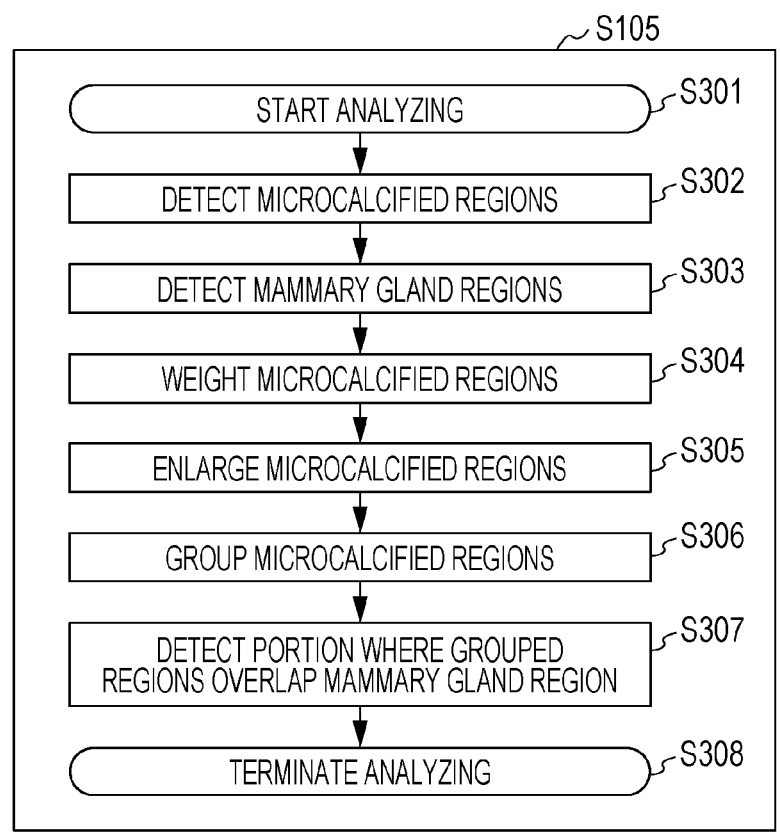

[Fig. 2C]
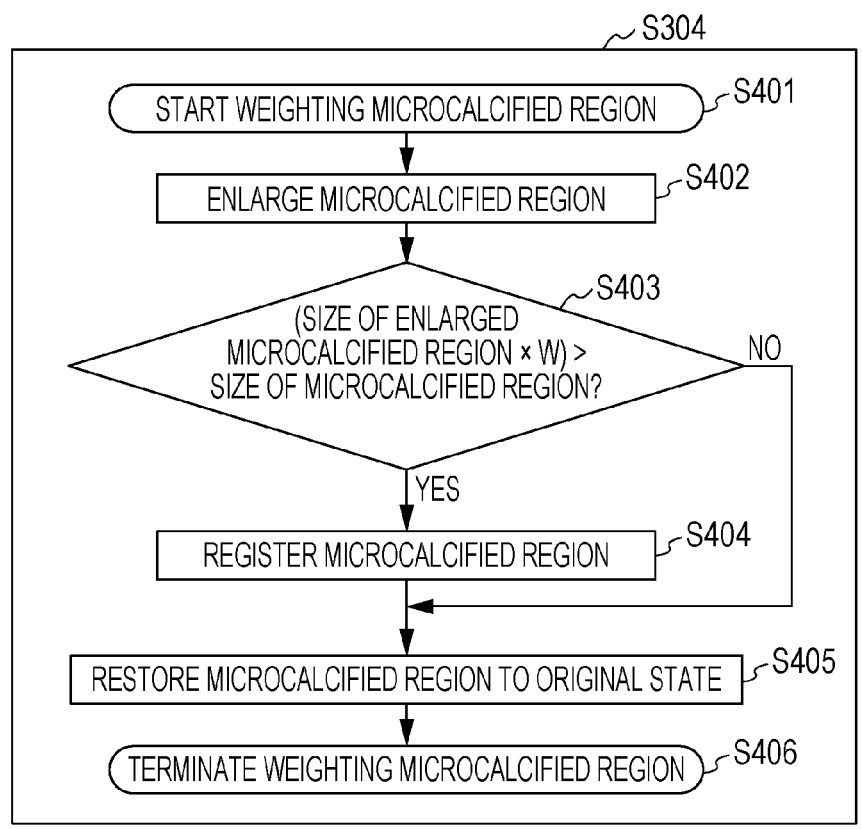

[Fig. 3]
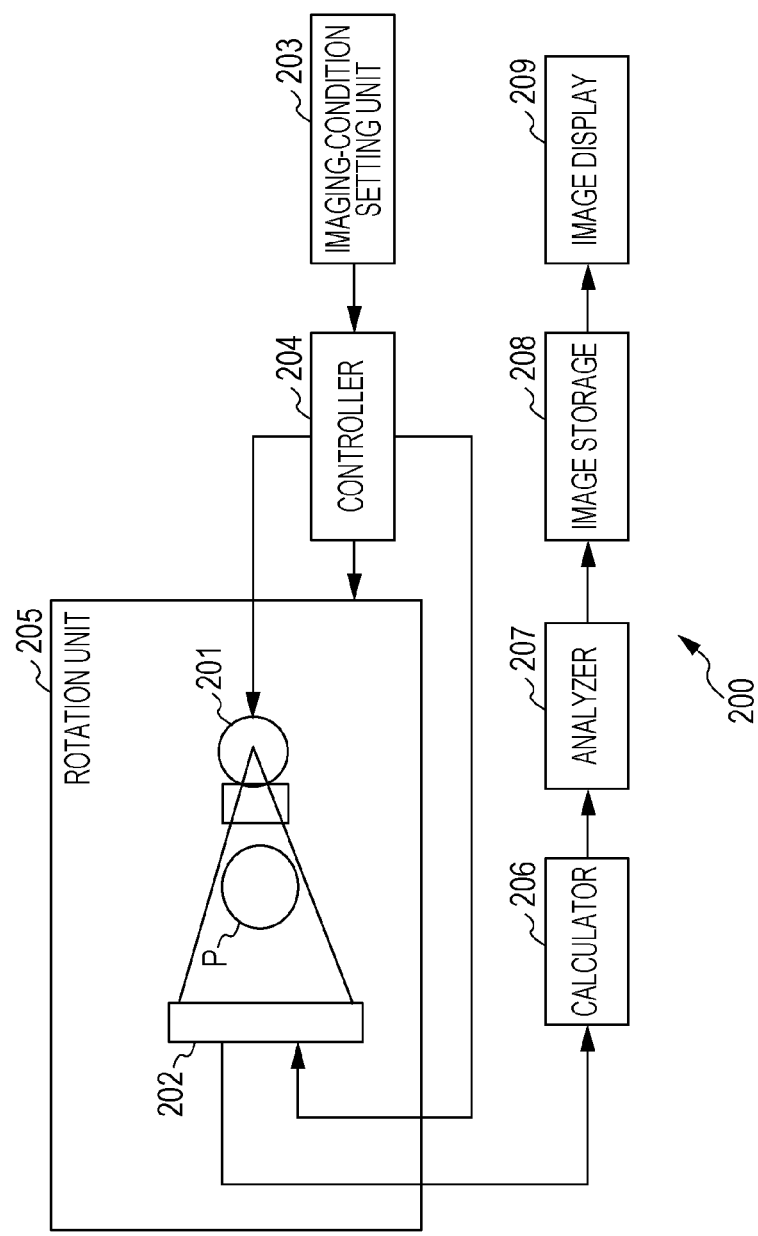

[Fig. 4A]
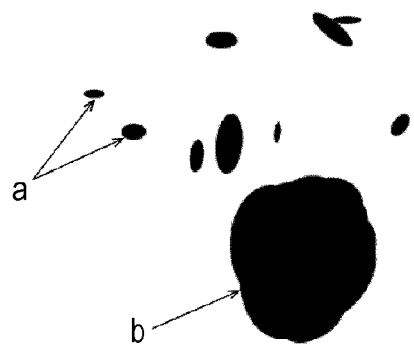
[Fig. 4B]
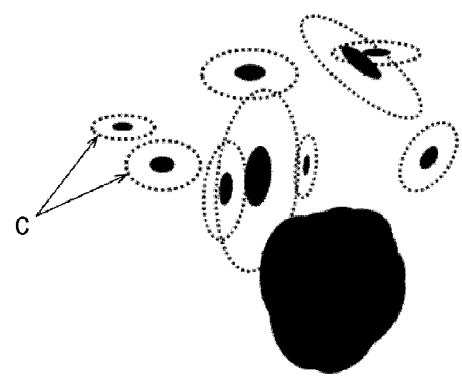
[Fig. 4C]
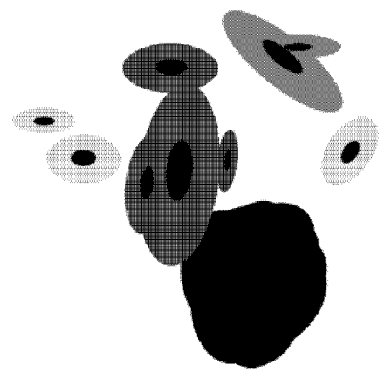

[Fig. 4D]
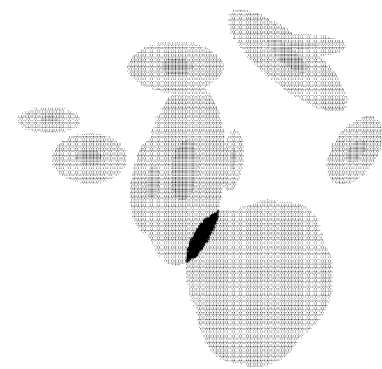
[Fig. 4E]
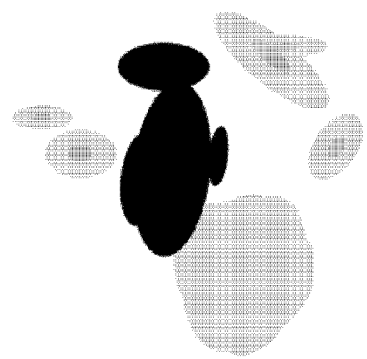

IMAGE PROCESSING APPARATUS AND RADIOGRAPHIC IMAGE DATA DISPLAY METHOD

TECHNICAL FIELD

The present invention relates to an image processing apparatus that generates radiographic image data from a captured breast image and a radiographic image data display method.

BACKGROUND ART

Diagnosis support apparatuses for improving the efficiency of diagnosis based on radiographic image interpretation are known. An apparatus disclosed by PTL 1 determines at least one of a display position, a shape, and a size of a detection frame in accordance with information on the distribution of candidate points of microcalcification shadows included in candidate regions of microcalcification shadows detected in a subject image and displays a result of detecting abnormal shadows. A calcification display apparatus disclosed by PTL 2 identifies pixel regions representing possibly calcified tissue, dilates, for each of the identified pixel regions, a corresponding region including the pixel region, combines the pixel regions pertaining to the dilated corresponding regions contiguously adjoining one another into one group, and displays the group with color or brightness according to the number of the pixel regions belonging to the group. In a method of outputting classification results of breast images disclosed by PTL 3, mammary gland regions representing mammary glands in breast images are extracted, and the breast images are classified into a plurality of categories in accordance with a size of the mammary gland region and displayed along with the category information.

CITATION LIST

Patent Literature

PTL 1: Japanese Patent Laid-Open No. 2003-310587
PTL 2: Japanese Patent Laid-Open No. 2016-22143
PTL 3: Japanese Patent Laid-Open No. 2005-65857

SUMMARY OF INVENTION

In breast cancer diagnosis, the state of microcalcification inside mammary glands is important. However, a microcalcified region formed inside mammary glands is difficult to identify in an image captured by mammography by using a diagnosis support apparatus of the related art.

The present invention provides an image display method by which a portion where a mammary gland region and a microcalcified region overlap each other can be intuitively identified.

Solution to Problem

A radiographic image data display method according to an aspect of the present invention includes detecting microcalcified regions and a mammary gland region from radiographic image data, and displaying the microcalcified regions and the mammary gland region on a single screen.

Further features of the present invention will become apparent from the following description of exemplary embodiments with reference to the attached drawings.

BRIEF DESCRIPTION OF DRAWINGS

FIG. 1 is a flowchart illustrating an operation of an X-ray imaging apparatus according to embodiments of the present invention.

FIG. 2A is a flowchart illustrating an image analysis process according to an embodiment of the present invention.

FIG. 2B is a flowchart illustrating an image analysis process according to another embodiment of the present invention.

FIG. 2C is a flowchart illustrating the image analysis process according to the other embodiment of the present invention.

FIG. 3 is a block diagram illustrating a configuration of a computed tomography (CT) apparatus according to the embodiments of the present invention.

FIG. 4A is a schematic illustration of the image analysis process according to the embodiments of the present invention.

FIG. 4B is a schematic illustration of the image analysis process according to the embodiments of the present invention.

FIG. 4C is a schematic illustration of the image analysis process according to the embodiments of the present invention.

FIG. 4D is a schematic illustration of the image analysis process according to the embodiments of the present invention.

FIG. 4E is a schematic illustration of the image analysis process according to the embodiments of the present invention.

DESCRIPTION OF EMBODIMENTS

Hereinafter, embodiments of the present invention will be described with reference to the drawings. Although a CT apparatus for breast imaging will be described as a radiographic imaging apparatus according to the embodiments of the present invention, the present invention may be applicable to other radiographic (for example, α-ray, β-ray, γ-ray, and the like), ultrasonic, or magnetic resonance images.

First Embodiment

FIG. 3 illustrates the entire configuration of a CT apparatus for breast imaging according to a first embodiment of the present invention as an X-ray imaging apparatus (an X-ray imaging system) 200. An X-ray irradiation unit 201 includes an X-ray generator (a vacuum tube), which generates an X-ray beam, and a collimator, which defines the angle of divergence of the X-ray beam generated by the X-ray generator. An X-ray detector 202, which is a flat panel detector (FPD) constituted by image sensors arranged in two dimensions, detects an X-ray beam that has passed through a subject P and reached detecting elements, and produces X-ray image data as radiographic image data. The X-ray image data is transmitted to a calculator 206.

An imaging-condition setting unit 203 has an imaging-condition input unit that receives imaging parameters such as a vacuum tube voltage and a vacuum tube current. The imaging parameters, which are input by an operator, determine a target X-ray dose with which the subject P is irradiated by the X-ray irradiation unit 201. The imaging-condition setting unit 203 transmits imaging-condition information based on the imaging parameters to a controller 204. The controller 204 coordinates and controls the X-ray irradiation unit 201, the X-ray detector 202, and a rotation unit 205 in accordance with the imaging-condition information. Based on a signal from the controller 204, the rotation unit 205 rotates the X-ray irradiation unit 201 and the X-ray detector 202, which are disposed inside the rotation unit 205, around the subject P (breast), which is the center of rotation.

Based on the X-ray image data transmitted from the X-ray detector 202, the calculator 206 reconstructs a CT image. The reconstructed CT image data is transmitted to an analyzer 207. The analyzer 207 transmits analyzed CT image data to an image storage 208. The image storage 208 saves received CT image data in a memory region and transmits the received CT image data to an image display 209. The image display 209 displays received CT image data on a screen.

The controller 204 and the calculator 206 are part of a computer, and data processing is executed by using a predetermined program. The calculator 206 and the analyzer 207 constitute an image processing apparatus.

A process from start to termination of imaging of the subject P will be described with reference to FIG. 1. This embodiment will illustrate a method by which a portion where microcalcified regions overlap a mammary gland region is identified in a CT image and the identified overlapping portion is displayed. If a tumor is found in the subject P, the mammary gland region may be replaced by a tumor region.

Step S101: An operator inputs imaging parameters such as a vacuum tube voltage (kV) and a vacuum tube current (mA) through the imaging-condition input unit.

Step S102: Based on the received imaging information, the controller 204 rotates the rotation unit 205, causes the X-ray irradiation unit 201 to irradiate the subject P with an X-ray beam under a predetermined condition, controls the X-ray detector 202, and starts acquiring X-ray image data.

Step S103: The controller 204 controls the X-ray irradiation unit 201 and terminates the X-ray irradiation.

Step S104: The calculator 206 reconstructs a CT image from the X-ray image data and transmits the reconstructed CT image data to the analyzer 207.

Step S105: The analyzer 207 analyzes a received CT image for microcalcified regions and mammary gland regions. Step S105 will be described with reference to FIG. 2A.

Upon start of step S105 (step S201), individual microcalcified regions are detected (step S202). Possible methods of detecting microcalcified regions include use of a threshold, contrast to the surrounding regions, a ring filter, and a texture analysis. Of these methods, the use of a threshold is relatively easy to handle. Subsequently, mammary gland regions are detected (step S203). The same methods may be used to detect mammary gland regions as the methods used to detect microcalcified regions, and the use of a threshold is relatively easy to handle in this case too. Detected microcalcified regions are enlarged to a predetermined size (step S204). A method to enlarge the regions will be described with reference to FIGS. 4A to 4E. In FIG. 4A, microcalcified regions a and a mammary gland region b are displayed. In FIG. 4B, the microcalcified regions a are enlarged to a predetermined size and denoted by regions c. It is assumed that the size of the enlarged microcalcified regions c is more than or equal to twice the size of the microcalcified regions a. Possible methods of enlarging regions include enlarging the original volume by a fixed amount repeatedly and performing dilation processing on the regions, but the former is relatively easy to handle. Of the enlarged regions c, microcalcified regions that overlap each other are grouped together as a collection (step S205). A portion where the enlarged microcalcified regions that have been grouped together overlap the mammary gland region b is detected (step S206). Step S105 is terminated with the information acquired in step S202 to step S206 retained (step S207).

Step S106: The image storage 208 saves the received CT image data in the memory region.

Step S107: The image display 209 displays the microcalcified regions a, the mammary gland region b, and the enlarged microcalcified regions c on the same screen using the received CT image data. Based on the analysis information acquired in step S105, the image display 209 adds color and brightness to each group in the displayed image data in accordance with the number of microcalcified regions included in the same group. FIG. 4C illustrates an example in which enlarged regions included in a group with a smaller number of microcalcified regions have colder colors and enlarged regions included in a group with a larger number of microcalcified regions have warmer colors. FIG. 4D illustrates an example in which an overlapping portion of the microcalcified regions that have been grouped together and the mammary gland region b is displayed with emphasis by adding at least one of color and brightness to the overlapping portion. FIG. 4E illustrates an example in which, when the microcalcified regions that have been grouped together and the mammary gland region b overlap, the microcalcified regions that have been grouped together are displayed with emphasis by adding at least one of color and brightness to the grouped microcalcified regions. The same color and brightness may be added to each of the detected microcalcified regions that have been grouped together. Then, the imaging process is terminated.

Further, for example, emphasized portions may be selected by a button operation or the like from microcalcified regions that have been grouped, mammary gland regions, microcalcified regions that have not been subjected to grouping processing, only overlapping portions of the regions mentioned above, and the like. In enlarged microcalcified regions that have been grouped together, microcalcified regions before enlarging may be displayed using color and brightness that differ from the color and brightness used for the portions other than the microcalcified regions before enlarging.

Second Embodiment

Next, a second embodiment of the present invention will be described. The second embodiment is different from the first embodiment in that microcalcified regions are weighted based on the shape thereof by the analyzer 207. While a microcalcified region is enlarged in the same shape in the first embodiment, a microcalcified region is enlarged to a spherical shape, and the size of the sphere is compared with the size of the microcalcified region before enlarging in this embodiment. Thus, the shape of the microcalcified region is determined, and superior information may be presented in diagnosis.

Hereinafter, step S105 will be described with reference to FIG. 2B. Processing in other steps is the same as in the first embodiment.

Step S105 is started (step S301). Microcalcified regions are detected (step S302). Mammary gland regions are detected (step S303). The microcalcified regions are weighted using a feature value (step S304). Step S304 will be described with reference to FIG. 2C. In step S401, weighting of a microcalcified region using a feature value is started. In step S402, the microcalcified region is enlarged. The microcalcified region is not enlarged in the same shape but enlarged to a sphere with a radius equal to the distance from the center of the microcalcified region to the farthest end of the microcalcified region from the center. In step S403, the size of the enlarged microcalcified region is multiplied by W, which may be any chosen value, and compared with the size of the microcalcified region before enlarging. If the microcalcified region before enlarging is smaller, the process proceeds to step S404. If not, the process proceeds to step S405. In step S404, information on the microcalcified region before enlarging is registered and retained. In step S405, the microcalcified region enlarged in step S402 is restored to the original state. In step S406, step S304 is terminated. When a feature value of a microcalcified region is obtained, a method of using a value such as degree of sphericity, which is determined by comparing the surface area of the microcalcified region with the surface area of a sphere with the same volume, is used. A plurality of feature values may be used simultaneously.

In the aforementioned embodiments, each of the microcalcified regions is enlarged, but a mammary gland region and a tumor region may also be enlarged similarly.

According to the embodiments of the present invention, more effective diagnosis is possible by displaying, with emphasis, a distribution of microcalcified regions that overlap a mammary gland.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-061535, filed Mar. 27, 2017, which is hereby incorporated by reference herein in its entirety.

REFERENCE SIGNS LIST

201 X-ray irradiation unit
202 X-ray detector
204 controller
207 analyzer

The invention claimed is:

1. A radiographic image data display method comprising:
  detecting microcalcified regions and a mammary gland region from radiographic image data; and
  displaying the microcalcified regions and the mammary gland region on a single screen,
  wherein the microcalcified regions are enlarged, and microcalcified regions whose enlarged regions overlap each other are grouped together as a collection, and
  wherein a portion where the microcalcified regions that have been grouped together overlap the mammary gland region is detected.

2. The radiographic image data display method according to claim 1, wherein the microcalcified regions are enlarged to a spherical shape.

3. The radiographic image data display method according to claim 1, wherein the portion where the microcalcified regions that have been grouped together overlap the mammary gland region is displayed with emphasis using at least one of color and brightness.

4. The radiographic image data display method according to claim 3, wherein an emphasized portion is selected from the microcalcified regions that have been grouped, the mammary gland region and the overlapping portion.

5. A non-transitory computer readable medium that stores a program that, when executed by a computer, causes the computer to execute the radiographic image data display method according to claim 1.

6. The radiographic image data display method according to claim 1, wherein when the microcalcified regions that have been grouped together and the mammary gland region overlap, the microcalcified regions that have been grouped together are displayed with emphasis by adding at least one of color and brightness.

7. An image processing apparatus comprising:
  a calculator that reconstructs computed tomography (CT) image data from X-ray image data acquired from an X-ray detector; and
  an analyzer that performs image processing on the CT image data, wherein the analyzer detects a microcalcified region and a mammary gland region in the CT image data and causes the microcalcified region and the mammary gland region to be displayed on a single screen of a display,
    wherein the microcalcified regions are enlarged, and microcalcified regions whose enlarged regions overlap each other are grouped together as a collection, and
    wherein a portion where the microcalcified regions that have been grouped together overlap the mammary gland region is detected.

8. An X-ray imaging system comprising:
  the image processing apparatus according to claim 7;
  an X-ray irradiation unit that irradiates a subject with an X-ray beam;
  an X-ray detector that detects the X-ray beam that has passed through the subject; and
  a rotation unit that rotates the X-ray irradiation unit and the X-ray detector with respect to the subject.

* * * * *